United States Patent

Hahn et al.

Patent Number: 6,061,641
Date of Patent: May 9, 2000

[54] METHOD FOR IMPROVING INSTRUMENT RESPONSE

[76] Inventors: David W. Hahn, 7528 Oxford Cir., Dublin, Alameda County, Calif. 94568; Kenneth R. Hencken, 2665 Calle Alegre, Pleasanton, Alameda County, Calif. 94566; Howard A. Johnsen, 5443 Celeste Ave.; William L. Flower, 5447 Theresa Way, both of Livermore, Alameda County, Calif. 94550

[21] Appl. No.: 08/956,520

[22] Filed: Oct. 23, 1997

Related U.S. Application Data

[60] Provisional application No. 60/029,309, Oct. 25, 1996.

[51] Int. Cl.$^7$ ......................................................... G01J 3/00
[52] U.S. Cl. .............................. 702/85; 702/69; 702/191; 356/318; 356/316
[58] Field of Search .................................. 702/85, 69, 79, 702/191; 356/316, 318, 346

[56] References Cited

U.S. PATENT DOCUMENTS

| | | | |
|---|---|---|---|
| 4,986,658 | 1/1991 | Kim | 356/318 |
| 5,526,110 | 6/1996 | Braymen | 356/316 |
| 5,751,416 | 5/1998 | Singh et al. | 356/318 |
| 5,847,825 | 12/1998 | Alexander | 356/318 |

OTHER PUBLICATIONS

Holtzclaw et al; Real–time optical measurement of Alkali Species in Air for Jet Engine Corrosion Testing; A Division of physical sciences Inc. pp. 1–7, Jan. 11–14, 1993.

Primary Examiner—Marc S. Hoff
Assistant Examiner—Bryan Bui
Attorney, Agent, or Firm—Timothy Evans

[57] ABSTRACT

This invention pertains generally to a method for improving the accuracy of particle analysis under conditions of discrete particle loading and particularly to a method for improving signal-to-noise ratio and instrument response in laser spark spectroscopic analysis of particulate emissions. Under conditions of low particle density loading (particles/m$^3$) resulting from low overall metal concentrations and/or large particle size uniform sampling can not be guaranteed. The present invention discloses a technique for separating laser sparks that arise from sample particles from those that do not; that is, a process for systematically "gating" the instrument response arising from "sampled" particles from those responses which do not, is dislosed as a solution to his problem. The disclosed approach is based on random sampling combined with a conditional analysis of each pulse. A threshold value is determined for the ratio of the intensity of a spectral line for a given element to a baseline region. If the threshold value is exceeded, the pulse is classified as a "hit" and that data is collected and an average spectrum is generated from an arithmetic average of "hits". The true metal concentration is determined from the averaged spectrum.

13 Claims, 4 Drawing Sheets

METHOD FOR IMPROVING INSTRUMENT RESPONSE

The following application claims priority to U.S. Provisional Application Ser. No. 60/029,309, filed Oct. 25, 1996.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

This invention pertains generally to a method for improving the accuracy of particle analysis under conditions of discrete particle loading and particularly to a method for improving signal-to-noise ratio and instrument response in laser spark spectroscopic analysis of particulate emissions.

Thermal processing, including incinerator and plasma processes, is a viable method for the treatment of a wide variety of materials including waste materials. Many feeds, however, contain quantities of metal compounds that cannot be destroyed during the primary treatment process, but instead must be removed from the effluent stream by conventional scrubbing techniques. Significantly, the Clean Air Act regulates eleven metals that have been identified as air toxins: antimony (Sb), arsenic (As), beryllium (Be), cadmium (Cd), chromium (Cr), cobalt (Co), lead (Pb), mercury (Hg), manganese (Mn), nickel (Ni), and selenium (Se). In view of the utility of thermal processing and the need for regulatory compliance, a technology for continuous monitoring of metal emissions would be desirable.

A candidate for such a continuous particle monitor can be based on a technique referred to as Laser Spark Spectroscopy (LASS) or Laser Induced Breakdown Spectroscopy (LIBS). French et al. in co-pending application (Ser. No. 08/228,974), incorporated herein by reference, disclose a LASS-based method and apparatus for analyzing particulate emissions from combustion systems. In particular, this system comprises a means for rapidly heating a particle or assemblage of particles to form a plasma, a means for collecting and transmitting light emitted by the plasma, a means for optically dispersing the light into wavelength components, a means for measuring the distribution of light intensity as a function of wavelength to produce spectral data, and a means for acquiring, analyzing, manipulating and displaying the spectral data. As disclosed by French, et al., this technique employs, a pulsed laser beam is focused in the effluent stream where the high energy and power densities of the beam generate an optical breakdown, also referred to as a laser spark or laser-induced plasma. If the laser beam is focused onto a particle, all species comprising the particle, including the metals of interest, are decomposed into excited atoms and ions. The spectral emission from these excited atoms are captured by standard optical elements and directed into a spectrometer where the emitted light is dispersed into wavelength components. Measurement of these components enables species identification, while the emission intensities provide a measure of the atomic concentrations.

The LASS system response to a specific metal can be calibrated to reflect the metal concentration, usually expressed in the units of $\mu g/acm$ (acm=actual cubic meter). In reality, the response corresponds to the actual mass of metal contained within the actual plasma volume. The plasma volume is typically $5 \times 10^{-5}$ cm$^3$. Instrument calibration can be accomplished using fine aerosol dispersions of known concentrations for each metal of interest. When the metals are dispersed on a length scale that is much smaller than the minimum plasma dimension (250 $\mu m$), each laser spark contains a representative metal sample, and multiple-shot averaging may be used to reduce single-shot experimental noise. Using such an approach, the LASS instrument can be calibrated and the instrument response, including minimum detectable concentrations, can be determined for various metals.

In combustion systems, however, the fate of metals is a complex phenomenon controlled by mechanisms such as particle entrainment, chemical interactions, vaporization, condensation, particle coagulation, and particle collection. Furthermore, in the effluent stack, where LASS monitoring would typically take place, most metals exist as either homogeneous or multi-species particulate. Under such discrete particle loading conditions, uniform metal sampling via LASS sampling is by no means guaranteed. In fact, the conditions of low particle density loading resulting from low overall metal concentrations and/or large particle sizes can be a limiting factor for the success of a LASS metal emissions monitor. What is needed, therefore, is a technique to deal specifically with the issues of variable particle loading and resulting poor instrument response.

SUMMARY OF THE INVENTION

Laser Spark Spectroscopy (LASS) forms the basis for a method for analyzing the composition of particles emitted from various manufacturing processes, particularly combustion systems. However, under conditions of low particle density loading (particles/m$^3$) resulting from low overall metal concentrations and/or large particle sizes, uniform sampling can not be guaranteed. The present invention discloses a solution for this problem namely, a technique for separating laser sparks that arise from sample particles from those that do not. The approach disclosed herein is based on a LASS technique which includes random sampling combined with a conditional analysis of each pulse. Applicants' invention, as noted above is based on the system of French, et al., and uses most of the same mechanical and optical elements. Applicants invention, however, is not a device but rather a method for using an apparatus like the French apparatus.

The instant invention teaches that a threshold value is determined for the ratio of the intensity of a spectral line for a given element, to a baseline region. If the threshold value is exceeded, the pulse is classified as a "hit" and that data is collected by a computer means as with the French system and an average spectrum is generated from an arithmetic average of "hits". The true metal concentration is determined from the averaged spectrum.

DETAILED DESCRIPTION OF THE INVENTION

Figure 1:
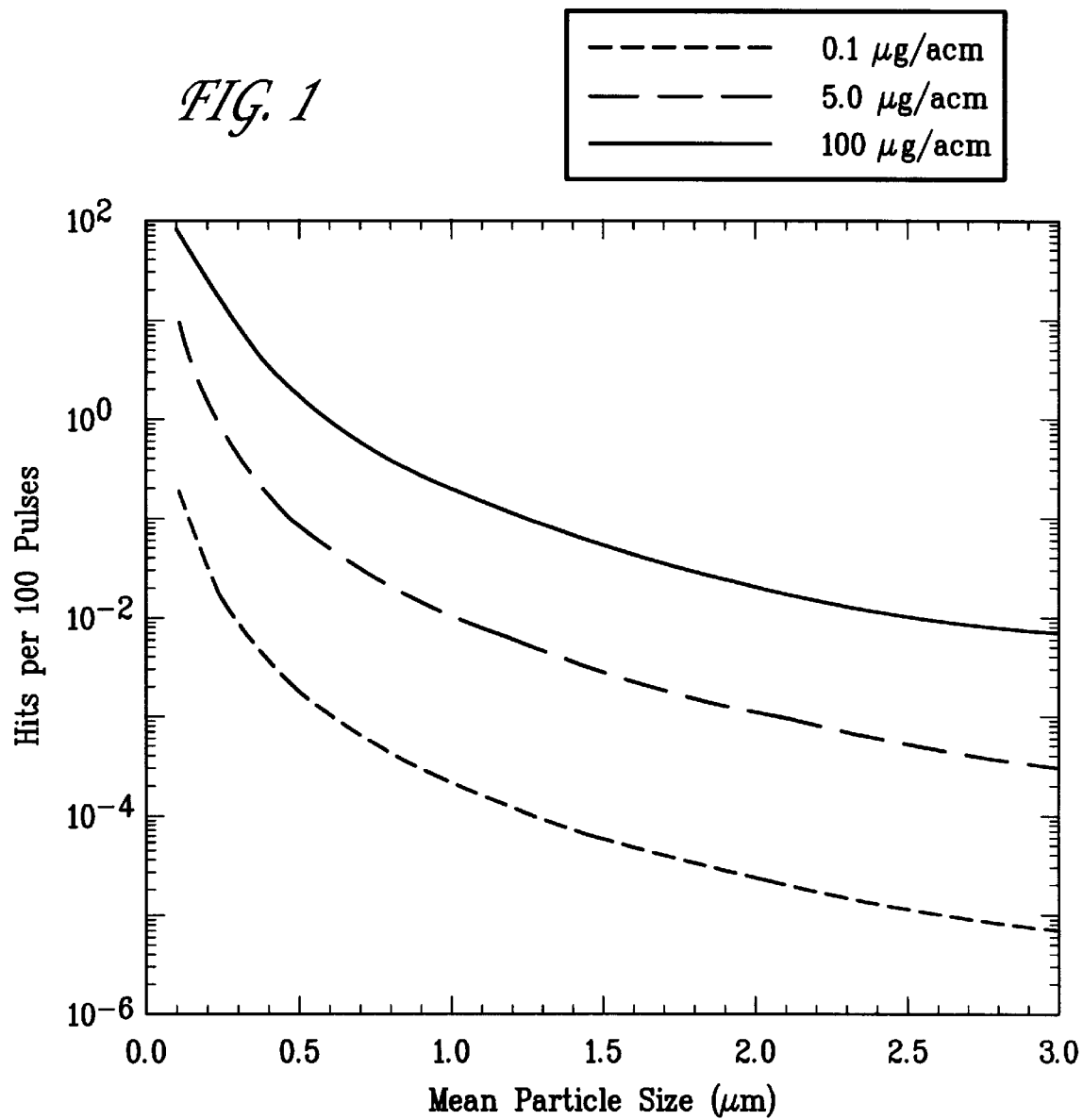
FIG. 1 illustrates the probability of sampling particles for three concentrations in air.

The invention disclosed herein relates generally to a method for greatly improving the signal-to-noise and instrument response to metals present under discrete particle loading conditions and particularly to the analysis of particulate matter in emissions sources by LASS. The random sampling and conditional analysis method described herein particularly enables the LASS technique to be used under conditions when the time-averaging mode would be expected to provide either a poor response or a non-detect response to metal concentrations in effluent streams.

The inventors have developed a novel approach, based on random sampling combined with the conditional analysis of each single laser pulse in an overall sequence of pulses, for improving the accuracy of LASS-based analysis of particulate emissions, wherein a ratio is calculated in real-time for each spectrum collected. The technique for improving the response discrimination of a signal detection instrument, can be summarized as comprising the steps of:

a.) detecting the random signal and dispersing that signal into an emission spectrum having a series of spectral lines above some background signal.

The new technique begins by generating light emissions as does French, et al., but then extends the approach by sampling large numbers of emissions, typically 100–500. As with French, et al., at least some of the light from each of the emissions is collected and optically dispersed by known spectrographic means to form an optical spectra for each emission.

b.) Electronically digitizing and storing the dispersed spectrum.

In order to provide a useable signal, the dispersed light from each spectra is first directed onto a pixelating mean such as a linear diode array. As is known in the signal processing arts, each diode array element, or "pixel," generates an analog output signal whose magnitude is proportional to the intensity of the light received by that pixel. Furthermore, it is known to calibrate the array and the spectrographic means with which it is associated so that the position location of any particular part of the dispersed signal (spectrum) along the length of the diode array is associated with a particular signal wavelength. The output of each of the diode elements (pixels) is passed to an analog-to-digital converter (ADC), which measures the analog signal (typically a voltage proportional to the relative light intensity measured by the pixel) and outputs an digital number corresponding to the relative strength of the signal measured by the diode elements. Since it is known in the art of ADC's to associate each channel of an ADC with a detecting element such as a diode pixel, the collected output of all the ADC channels correspond, therefore, to a sequence of ordered digital data "words" forming a digitized spectra. Comparisons, therefore, may be made between spectra and between pixels comprising separate spectra.

c.) Zeroing first and second electronic register;

It is well known in developing computer algorithm techniques to prepare a counter and arithmetic registers by first initialize or "zero" the registers in order to avoid corrupting new data with spurious content which may have been retained in the register from earlier calculation.

d.) electronically adding the spectra to the contents of the first electronic register; and e.) repeating said steps a.), b.) and d.) until reaching a pre-established number of spectra have been summed.

All of the collected spectra are separately summed to provide an arithmetic time-averaged spectrum of the collected LASS spectra. This is done using well known computer algorithmic techniques wherein a counter register and an arithmetic computer register are first emptied or "zeroed" as in step (c.), incrementing the counter register by 1 and adding the first of the stored spectra to the arithmetic register Step (d.). This process is continued by incrementing the counter register by 1 and then adding each succeeding stored spectra until all have been summed step (e.).

f.) Computing and electronically storing an arithmetic average of the summed spectra thereby providing a time-averaged spectrum.

Spectra summing is performed pixel-by-pixel. A time-averaged spectrum is generated by dividing the contents of the arithmetic register by the contents of the counter register.

g.) Providing a known spectrum of an element of interest for comparison.

As provided by French, et al. it is known to provide a "look-up" table of spectra for comparison.

h.) Selecting an analysis region common to both the time-averaged spectrum and the known spectrum.

From the comparison, an analysis region is established on the time-averaged spectrum which includes both a region containing a spectral line of interest and a baseline region which is proximate but well removed form the chosen spectral line, and which does not include interfering spectral lines.

i.) Computing a signal threshold value within the analysis region of the time averaged spectrum.

The ratio is defined as the average intensity of several pixels (3 or 5 typically) centered about the expected metal spectral line, divided by the average of several pixels (5 to 11 typically) in a baseline region well removed from any species line emissions. These two groups of pixels define first and second bands, respectively, within the analysis region and the ratio obtained provides a general measure of the signal-to-noise within a limited region around the spectral line of interest.

Once this signal ratio has been established, an threshold value can be computed which will be used for later comparison of individual spectra to determine whether any particular spectra exhibits a signal which is sufficiently in excess of the background "noise" to qualify as exhibiting evidence of the present of the line of interest, i.e., a "hit.".

A threshold value for the ratio is selected that enables each laser pulse and spectrum to be classified as either a hit (exceeds threshold) or a miss. The threshold value is most easily and reliably set by first recording a time-averaged spectrum for a number of sequential pulses, nominally 100. If the metal line of interest is weak or not apparent in the time-averaged spectrum, then conditional analysis is required and the ratio, as discussed above, is calculated for the time-averaged spectrum. The time-averaged spectrum is also useful for selecting an appropriate baseline region to use for the ratio calculation. A threshold value can then be selected using the ratio value of the time-averaged spectrum. An approach that can be employed is to set the threshold value to 25% greater than the ratio of the time-averaged spectrum. For metals with particularly strong emissions, beryllium for example, the threshold can be set higher for better shot to shot discrimination.

j.) Repeating said steps a.) and b.) to provide a spectrum for analysis.

After establishing a threshold value the conditional analysis can be performed using new spectra data.

k.) Performing a conditional analysis in said analysis region of said analysis spectra which comprises the steps of:

i.) computing a signal response ratio for each of the stored spectra;

ii.) comparing the signal response ratio with the signal threshold value; and iii.) selecting only those said spectra whose signal response ratio exceeds the signal threshold value.

The signal response intensity within the first band of each new spectra is compared to the threshold value. Each spectra is designated as either exhibiting or not exhibiting a "hit" depending on whether the signal response within the first band exceeds the threshold value.

l.) Electronically adding the selected spectra to said contents of the second electronic register;

m.) repeating steps j.) through l.) until a second pre-established number of spectra have been analyzed; and n.) computing an arithmetic average spectrum of said summed selected spectra contained within the second electronic register.

Those spectra which exhibit "hits" are added as before to provide a second arithmetic averaged spectra. This second spectrum, however, is selective, or "conditional," and is based on evidence of a signal above a background signal within a specific region or bandwidth and corresponds to those spectra which . What results is a spectrum, averaged from only those spectra which appear to include the emission spectra of a particle or particles having the chosen spectral line. The process of computing the second averaged spectrum is identical to the process for computing the time-averaged spectrum in steps (a.) through (f.) above, with the exception that only those spectra exhibiting evidence of having a "hit" are summed.

Figure 2:
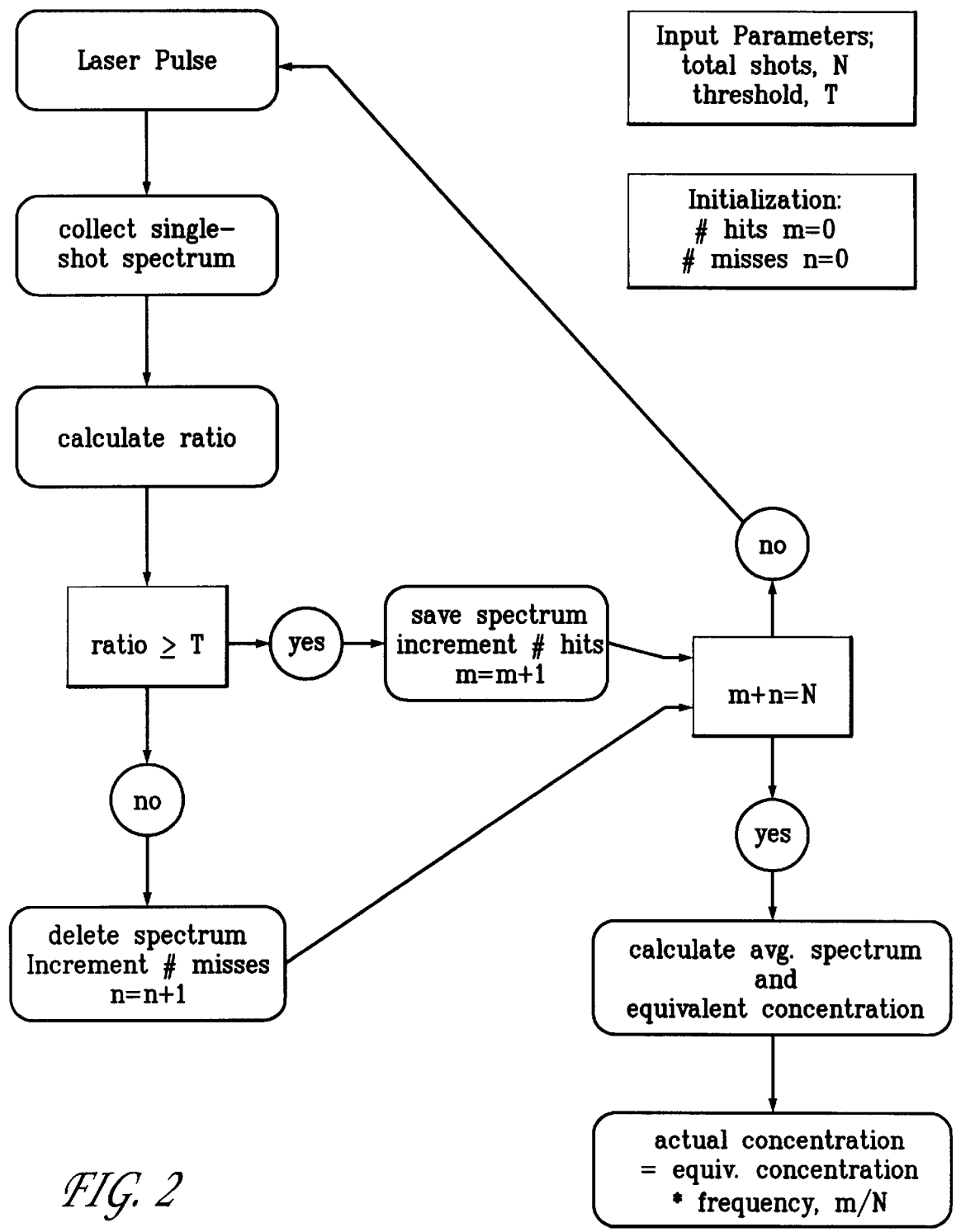
FIG. 2 illustrates the process for calculating metal concentrations employed by the present invention.

Once an appropriate ratio and threshold have been identified, the data analysis can be as set forth in FIG. 2 which shows a flow chart of a random sampling and conditional analysis algorithm useful for determination of metal concentrations under discrete particle loading conditions. The LASS system is set for a total number of pulses (nominally 100 to 500). A spectrum is recorded for each laser pulse and then classified as a hit or miss based on the calculated ratio and predetermined threshold. When a pulse is classified as a miss, the shot number is recorded and the spectrum is discarded. When a pulse is classified as a hit, the shot number and entire spectrum are recorded. After the total number of desired shots are completed, an average spectrum is generated based on the arithmetic average of the spectra recorded for all hits. An equivalent metal concentration is then calculated using the same methods as with any time-averaged LASS technique, typically based on intensity information. The true or actual metal concentration is then calculated from the product of the equivalent hit concentration and the frequency of hits (i.e., number of hits/total number of pulses).

A LASS-based system running at about 6 Hz allows a 100 pulse sequence to be completed in about 15 seconds. Such a system enables true real-time analysis. The system can also be operated in a conventional time-averaging mode by selecting an appropriate threshold (e.g., a negative value) such that every laser pulse is classified as a hit.

It is noted that by running the system at a fixed frequency, about 6 Hz, we achieve a random sample selection. This corresponds spatially to samples separated by about 15 cm each, for a nominal effluent duct flow of 1 m/s. By randomly sampling at a fixed rate, we can expect the frequency of hits to be representative of the true particle loading for a sufficient number of hits. This scheme eliminates a significant source of sample bias that can be introduced by trying to actively trigger the spark based on a priori particle detection. In other words, any attempt to detect particles in the target volume (e.g., using light scattering) and then initiate a laser spark would be prone to both particle size biases and to particle species biases.

Typically LASS instruments and, in particular LASS-based particulate emissions monitors, such as that described in co-pending Ser. No. 08/228,974, operate in a time-averaging mode. Specifically, either 25, 100, or 200 laser pulses (i.e., sparks) typically are collected and averaged to produce a representative spectral signal. The averaging technique is very useful for eliminating signal shot noise. For our current sampling rates, these correspond to sampling times less than one minute, meeting the requirement for real-time analysis. However, our calculations demonstrated that for metal concentrations and particle size ranges expected within the normal range of effluent streams, the probabilities of sampling particles can become limiting (see FIG. 1). For example, at a metal concentration of 100 $\mu$g/acm, less than 5% of the laser pulses would be expected to sample particles, assuming an average particle diameter of 0.5 $\mu$m. Depending on the signal response of a particular metal, these numbers may or may not be sufficient for time-averaging of the total laser pulses. However, for an average metal concentration of 5 $\mu$g/acm, which is on the order of expected effluent levels for many metal species of interest, approximately 1000 laser pulses would be expected to sample a single particle (0.1% sample rate). Time-averaging of metal signals with a 0.1% hit rate would reduce the signal-to-noise ratio well below the detection threshold. In addition, several particles alone would not be expected to represent a distribution of particles and could not be used to accurately determine average metal concentrations. To avoid these problems, and thereby to improve the accuracy of LASS particle analysis, the present invention discloses a technique that enables the separation of laser sparks that sample metals (i.e., "hits" on metal particles) from those laser pulses that sample no metal, "misses."

EXAMPLE

In order to demonstrate the effectiveness of the method disclosed herein for analysis of particle emissions from a combustion system, the inventors conducted a test at the U.S. Environmental Protection Agency's Rotary Kiln Incinerator (RKIS) at Research Triangle Park, N.C. during April 1996. During the field-test we were able to collect a series of 100 sequential laser pulses for several metal loading concentrations. These 100 shot sequences were then analyzed to test our algorithm. In FIGS. 3–6 we present examples from our first set of data analysis, in which spectra were examined for the presence of cadmium using the 226.5 nm line.

Figure 3:
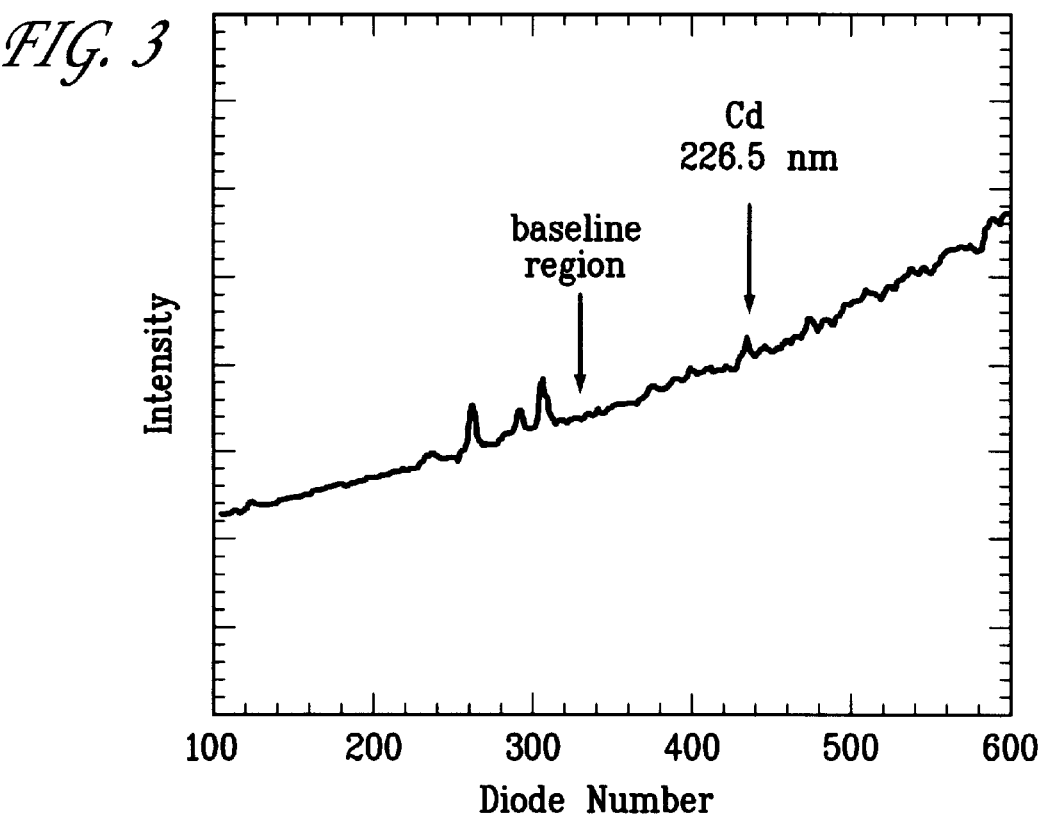
FIG. 3 is a averaged spectrum showing a weak Cd peak.
Figure 4:
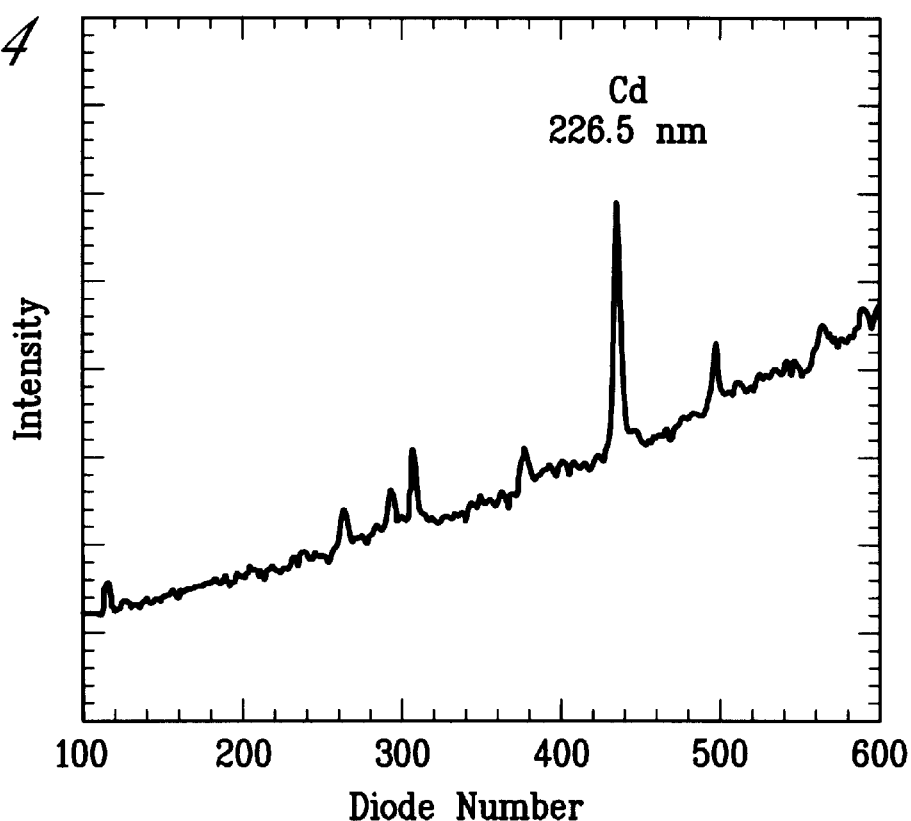
FIG. 4 shows the Cd peak in the spectrum of the 18 spectra containing only Cd hits.

A series of 99-shot averages were collected using a spectral window centered at 230 nm. This overlapped the Cd emission line at 226.502 nm, a strong line that is free from interference with other species that were present in the effluent stream at RKIS. FIG. 3 is the spectrum averaged over 297 laser pulses (corresponding to three series of 99 shots each) collected within a 6 minute time period. The Cd line at 226.5 nm is visible, but weak, in the time-averaged spectrum. The accurate determination of metal concentrations is difficult from such weak signals. A suitable baseline region free from interference was selected and is also labeled in FIG. 3. The ratio from the 297-shot average was calculated (using 3 pixels about the 226-nm peak, and 11 pixels near 223 nm for the baseline) and equaled 1.60. A threshold value of 25% above the 1.60 average value was established (threshold=2.0), and the single-shot spectra were all examined. From the 297 laser pulses, 18 spectra were identified as containing Cd hits. The average of the 18 hits are plotted in FIG. 4. The Cd line at 226.5 nm is much more pronounced in this spectrum as compared to the preceding figure.

Figure 5:
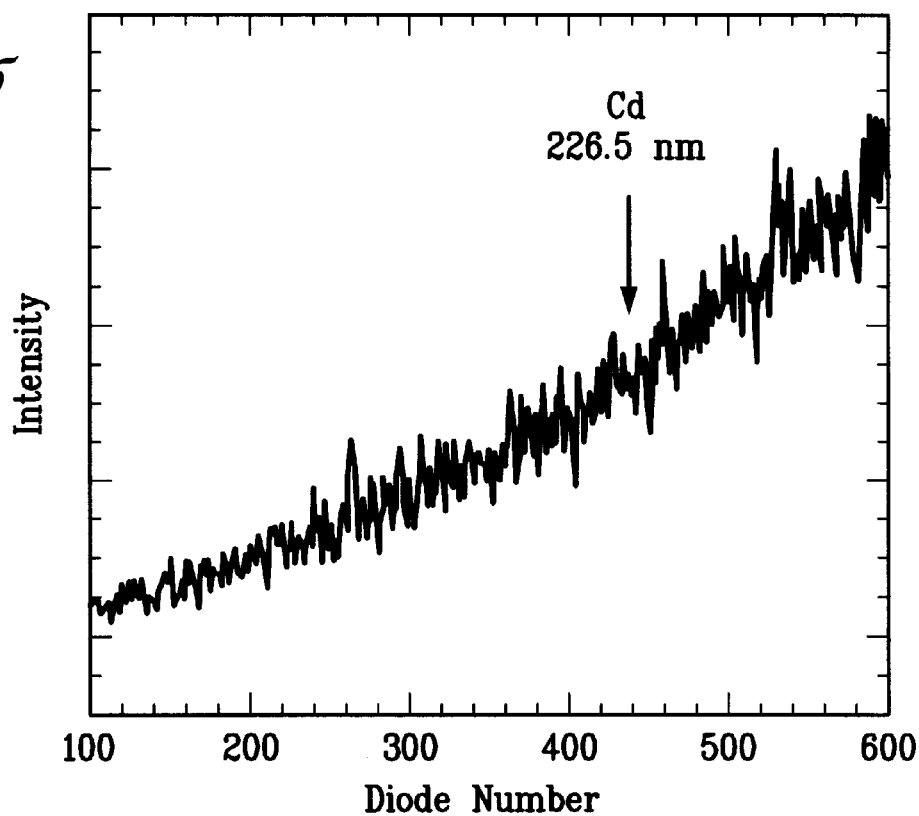
FIG. 5 shows a single laser shot spectrum for a particle miss.
Figure 6:
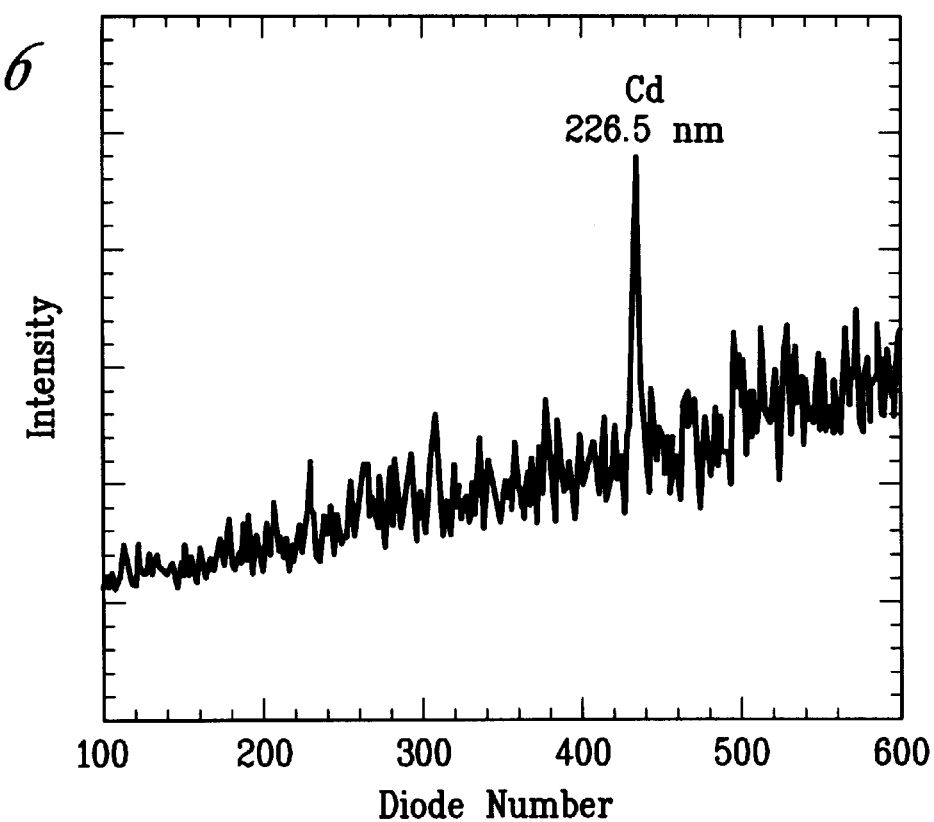
FIG. 6 shows a single laser shot spectrum for a Cd particle hit.

The equivalent concentration of Cd calculated from the average-hits spectrum is 194.7 $\mu$g/dscm,. (dscm=dry standard cubic meter). This concentration was then adjusted by multiplying by the frequency of hits, a value equal to 6.06% or 18/297. The resulting average concentration of metal for the 6 minute sample interval was 11.8 $\mu$g/dscm. During the test period, sample probes were also inserted near the LASS test region and metal concentrations were subsequently determined using the EPA Reference Method 60, formerly referred to as Method 29. For a one-hour sample period overlapping the LASS sample period, the EPA Method 60 cadmium concentration was reported as 10.7 $\mu$g/dscm. This number is in excellent agreement with the LASS value calculated using the conditional signal analysis algorithm described herein, namely 11.8 $\mu$g/dscm. FIGS. 5 and 6 contain the single-shot spectrum for a typical laser pulse "miss" and "hit," respectively. The discrete nature of the Cd LASS signal is apparent for these two individual pulses.

What is claimed is:

1. A method for improving the response discrimination of a signal detection instrument, the method comprising the steps of:
   a.) detecting and dispersing a random signal, said dispersed signal comprising an energy emission spectrum, each said spectrum further comprising a background signal intensity and a one or more discrete spectral lines, said lines consisting of sharp peaks in said background signal intensity, each said peak having an absolute signal intensity greater than said background signal intensity;
   b.) electronically digitizing and storing each said spectrum;
   c.) repeating steps a.) and b.) until a predetermined number of spectra have been stored;
   d.) computing a time-averaged signal spectrum comprising an arithmetic average of said plurality of stored spectra;
   e.) providing a known spectrum for comparison, said known spectrum having a known spectral line;
   f.) selecting an analysis region common to both said plurality of stored spectra and to said known spectra, said region chosen to contain said known spectral line;
   g.) computing a signal threshold value in said analysis region of said time-averaged spectrum; and
   h.) performing a conditional analysis in said analysis region in each of said stored spectra, said analysis for preferentially selecting those said spectra having a signal intensity value which exceeds said signal threshold value.

2. The method of claim 1 wherein the step of computing a signal threshold value further comprises the steps of:
   a.) computing a signal response ratio in said analysis region, said ratio consisting of a first average signal intensity, measured across a first region of said time-averaged spectrum, divided by a second average signal intensity, measured across a second region of said time-averaged spectrum, said first region centered over said known spectral line, said second region selected away from said known spectral line so as not to contain said first region; and
   b.) multiplying said signal response ratio by a factor of at least about 1.25, thereby providing said signal threshold value.

3. The method of claim 1 wherein the step of performing a conditional analysis further comprises the steps of:
   a.) computing a signal response ratio for each of said stored spectra in said analysis region;
   b.) comparing said signal response ratio with said threshold value;
   c.) summing all said stored spectra exhibiting a signal response ratio greater than said threshold value and discarding all other said stored spectra;
   d.) repeating the steps a.) through c.) until all said stored spectra have been analyzed; and
   e.) computing an arithmetic average spectrum of said summed spectra.

4. The method of claim 1 wherein said predetermined number is about between 100 and 500.

5. The method of claim 1 wherein said random signal is measured as either a frequency or a wavelength.

6. The method of claim 1 wherein the step of detecting comprises a spectrometer, said spectrometer having means for signal dispersion, said spectrometer further having a detector means comprising a linear diode array, said array comprising a plurality of detecting elements.

7. The method of claim 6 wherein said means for signal dispersion comprises a grating, said grating capable of dispersing said random signal sufficiently to resolve at least one said spectral line.

8. A method for improving the response discrimination of a signal detection instrument, the method comprising the steps of:
   a.) detecting and dispersing a random signal, said dispersed signal comprising an energy emission spectrum, said spectrum further comprising a background signal intensity and a plurality of discrete spectral lines, said lines consisting of sharp peaks in background signal intensity, each said peak having an absolute signal intensity greater than said background signal intensity;
   b.) electronically digitizing and said spectrum;
   c.) zeroing a first and a second electronic register;
   d.) electronically adding said spectra to said contents of said first electronic register;
   e.) repeating said steps a.), b.) and d.) until reaching a first predetermined number of spectra have been summed;
   f.) computing and electronically storing a time-averaged signal spectrum, said time-average spectrum comprising an arithmetic average of said predetermined number of summed spectra;
   g.) providing a known spectrum for comparison, said known spectrum having a known spectral line;
   h.) selecting an analysis region common to both said time-averaged spectrum and said known spectrum, said analysis region chosen to contain said known spectral line;
   i.) computing a signal threshold value in said analysis region of said time-averaged spectrum;
   j.) repeating said steps a.) and b.);
   k.) performing a conditional analysis in said analysis region of said spectra, wherein the step of performing a conditional analysis further comprises the steps of:
      i.) computing said signal response ratio for said stored spectra;
      ii.) comparing said signal response ratio with said threshold value;

iii.) selecting those said spectra having a signal intensity value which exceeds said signal threshold value;

l.) electronically adding said selected spectra to said contents of said second electronic register;

m.) repeating steps j.) through l.) until a second predetermined number of spectra have been analyzed; and n.) computing an arithmetic average spectrum of said summed selected spectra.

9. The method of claim 8 wherein the step of computing a signal threshold value further comprises the steps of:

a.) computing a signal response ratio in said analysis region, said ratio consisting of a first average signal intensity, measured across a first region of said time-averaged spectrum, divided by a second average signal intensity, measured across a second region of said time-averaged spectrum, said first region centered over said known spectral line, said second region selected away from said known spectral line so as not to contain said first region; and b.) multiplying said signal response ratio by a factor of at least about 1.25, thereby providing said signal threshold value.

10. The method of claim 8 wherein said first predetermined number is about between 100 and 500.

11. The method of claim 8 wherein said random signal is measured as either a frequency or a wavelength.

12. The method of claim 8 wherein the step of detecting comprises a spectrometer, said spectrometer having means for signal dispersion, said spectrometer further having a detector means comprising a linear diode array, said array comprising a plurality of detecting elements.

13. The method of claim 12 wherein said means for signal dispersion comprises a grating, said grating chosen to dispersing said random signal sufficiently to resolve at least one of said spectral lines.

* * * * *